United States Patent
Haacke et al.

(10) Patent No.: US 6,676,651 B2
(45) Date of Patent: Jan. 13, 2004

(54) URETER DRAINAGE DEVICE

(75) Inventors: Claus Haacke, Melsungen (DE); Juergen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 10/083,112

(22) Filed: Feb. 27, 2002

(65) Prior Publication Data

US 2002/0123739 A1 Sep. 5, 2002

(30) Foreign Application Priority Data

Mar. 2, 2001  (DE) ..................................... 201 03 653 U

(51) Int. Cl.$^7$ ............................................... A61M 5/00
(52) U.S. Cl. ....................................... 604/533; 604/905
(58) Field of Search ........................ 604/523, 533–539, 604/905; 285/346

(56) References Cited

U.S. PATENT DOCUMENTS

| | | | | |
|---|---|---|---|---|
| 4,326,518 A | * | 4/1982 | Williams ..................... | 604/410 |
| 4,551,146 A | * | 11/1985 | Rogers ....................... | 604/403 |
| 4,723,948 A | * | 2/1988 | Clark et al. ................. | 604/533 |
| 4,895,570 A | * | 1/1990 | Larkin ........................ | 604/411 |
| 4,963,129 A | | 10/1990 | Rusch | |
| 4,963,133 A | * | 10/1990 | Whipple ...................... | 604/533 |
| 5,195,994 A | * | 3/1993 | Dieringer .................... | 604/534 |
| 5,199,947 A | * | 4/1993 | Lopez et al. ................. | 604/518 |
| 5,247,942 A | * | 9/1993 | Prather et al. ............... | 600/585 |
| 2002/0010437 A1 | * | 1/2002 | Lopez et al. ................. | 604/256 |

FOREIGN PATENT DOCUMENTS

| | | | | |
|---|---|---|---|---|
| EP | 0 752 251 A2 | | 1/1997 | |
| GB | 2 071 247 A | * | 9/1981 | ........... F16L/19/00 |

* cited by examiner

*Primary Examiner*—Weilun Lo
*Assistant Examiner*—Michael G. Bogart
(74) *Attorney, Agent, or Firm*—Diller, Ramik & Wight

(57) ABSTRACT

In a ureter drainage device comprising a ureteral catheter (10), a sliding hose (12) to be coupled to the proximal end of the ureteral catheter (10), and a control hose (18) to be mounted over the sliding hose (12), it is provided that the ureteral catheter (10) and the sliding hose (12) comprise mutually engaging coupling elements (33,38). At least one coupling element (38), provided on the sliding hose (12), is radially outwardly biased in the release direction and retained in the engagement position by the control hose (18) covering this coupling element (38).

5 Claims, 3 Drawing Sheets

URETER DRAINAGE DEVICE

The present invention relates to a ureter drainage device comprising a ureteral catheter, a sliding hose to be coupled to the proximal end of the ureteral catheter, and a control hose to be mounted over the sliding hose.

BACKGROUND OF THE INVENTION

Ureteral catheters, which are also referred to as dual J-stents or in-dwelling ureter splints, are hose-shaped aids for discharge of the urine from the renal pelvis into the urinary bladder in cases where the ureter is not sufficiently permeable anymore. The ureteral catheters which are presently in widespread use have both of their ends formed with involutions. The involution in the renal pelvis has a smaller diameter while the involution of the bladder has a larger diameter. For placing the catheters through the urethra and the bladder, use is made of a cystoscope. The involutions of the catheter have to be straightened into a linear orientation so that the catheter will fit through the cystoscope working channel. This straightening of the catheter is carried out by means of a guide wire. If the tip of the catheter comprises a closed cap, the guide wire is set from the bladder-side end. If the guide wire is already arranged in the ureter, the straightening and subsequent upward shifting of the catheter into the renal pelvis is made possible in that the catheter tip is open and of an integral conical shape. Since the ureteral catheter serves for internal splintage and its draining end region extends only to a position within the bladder, the ureteral catheter remaining within the patient's body has to be shifted off the guide wire. This is accomplished by use of a sliding hose.

In certain cases where the ureter follows a considerably winding course or in case of very narrow ureter stenoses, a firm but detachable connection between the urethral catheter and the sliding hose would be suitable because such a connection would allow not only for shifting but also for pulling and rotating movements of the catheter.

U.S. Pat. No. 4,963,129 describes a ureter drainage device with shifting hose. The shifting hose connects to the urethral catheter via a coupling device comprising two interengaging coupling elements. Securement of the coupling device in the engaged position is performed by the guide wire. When the guide wire is pulled out, the sliding hose is detached from the ureter hose.

EP 0 752 251 A1 describes a ureter drainage device wherein the proximal end of the ureteral catheter is connected to a sliding hose through frictional engagement. Extending in the sliding hose is a control hose adapted to be advanced for releasing the frictional engagement and separating the ureteral catheter from the sliding hose.

It is an object of the invention to provide a ureter drainage device wherein the ureteral catheter is reliably held in position on the sliding hose for shifting, pulling and rotating movements during advancement, irrespective of whether a guide wire has been inserted.

SUMMARY OF THE INVENTION

In the ureter drainage device according to the instant invention, the ureteral catheter and the sliding hose comprise mutually engaging coupling elements. At least one of coupling element, provided on the sliding hose, is radially outwardly biased in the release direction and is retained in the engagement position by the control hose covering said one coupling element.

The invention allows for the use of the present catheter placement techniques such as the Seldinger technique and the retrograde technique. Using the invention, the decoupling of the ureteral catheter from the sliding hose can be performed easily and by application of a defined force. This is effected by two mutually engaging coupling members which are held in engagement by the outer control hose. This arrangement obviates the need for an internal guide wire for fixing the two members. At least one of the coupling elements of the sliding hose is subjected to an inherent radial outward bias in its release direction while being retained by the sliding hose so as to remain engaged with the proximal end of the ureteral catheter. In this manner, pulling forces as well as shifting and rotational forces can be transmitted. To release the connection, the control hose is withdrawn on the sliding hose, causing the coupling element to spread apart under the effect of the bias and thus to release the ureteral catheter.

According to a preferred embodiment of the invention, it is provided that the coupling element of the sliding hose comprises at least one distally projecting leg with a hook provided on its end, and that the coupling element of the ureteral catheter is formed with a recess for receiving the hook.

Preferably, the coupling element of the sliding hose is formed as a barb which, when sliding on the ureteral catheter, will snap into a locked position in a recess of the catheter. This barb is of a saw-tooth design comprising an inclined flank and an upright flank.

According to another preferred embodiment of the invention, there is provided a handling means comprising two grip portions arranged for displacement in the longitudinal direction and being biased to move away from each other in the longitudinal direction. One of the grip portions is connected to the sliding hose and the other grip portion is connected to the control hose. The grip portions are pressed away from each other by a spring means, with the control hose being urged into the advanced position to cover and lock the coupling device. When the grip portion connected to the control hose is retracted against the spring force, the control hose will release its grip on the coupling device and thus permit disengagement thereof. This allows for easy handling and even for single-handed operation of the drainage device for disengagement of the coupling device.

An embodiment of the invention will be described in greater detail hereunder with reference to the accompanying drawings.

DESCRIPTION OF THE PREFERRED EMBODIMENTS

Figure 1:
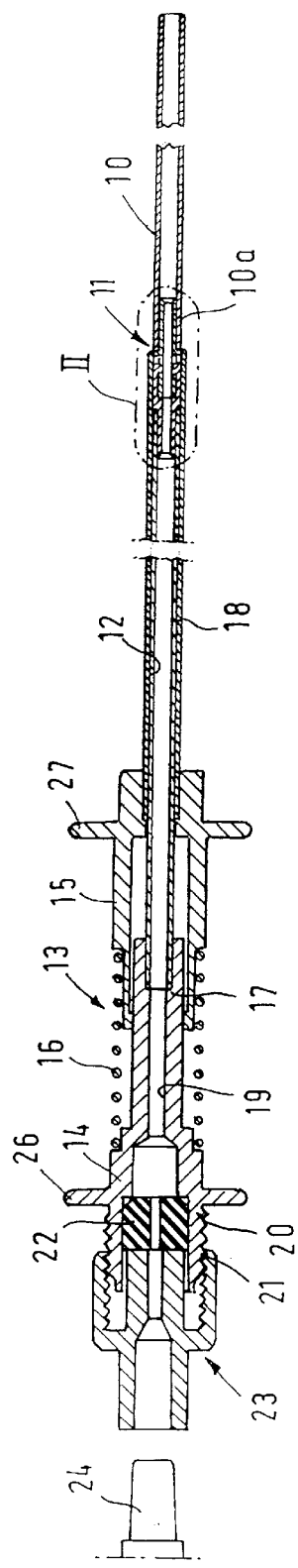
FIG. 1 is a longitudinal sectional view of the drainage device in the condition wherein the urethral catheter is being inserted into the body.

The ureter drainage device comprises a ureteral catheter 10 which consists of a flexible hose and in the relaxed condition has both of its ends formed with an involution. In the drawings, ureteral catheter 10 is illustrated in its linear stretched condition and without these end-side involutions.

The proximal end of ureteral catheter 10 is connected via a coupling device 11 to a sliding hose 12 forming an extension of ureteral catheter 10. The proximal end of sliding hose 12 is connected to a first grip member 14 and a handling device 13. On the first grip member 14, a second grip member 15 is arranged for longitudinal displacement. A spring 16 is provided to urge the two grip members 14 and 15 away from each other in axial directions, the movement of the second grip member 15 being delimited by a stopper 17.

Figure 3:
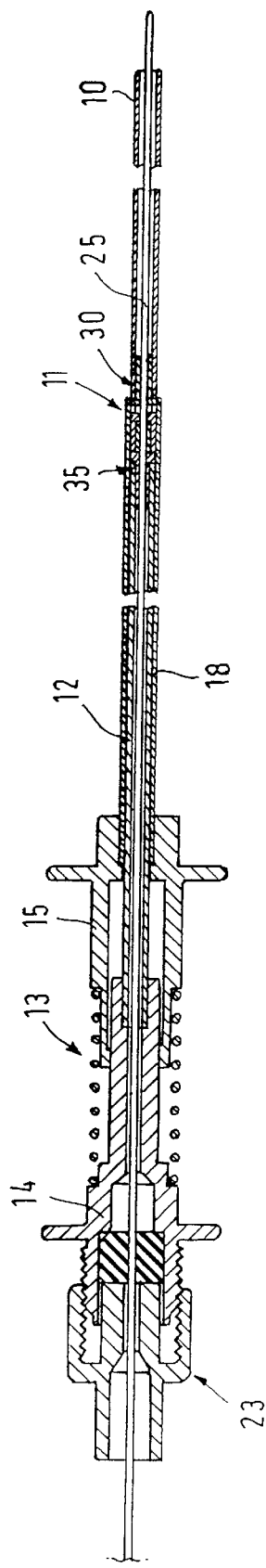
FIG. 3 is a longitudinal sectional view of the device with inserted guide wire.

The second grip member 15 has a control hose 18 attached thereto which surrounds the sliding hose 12. By moving the second grip portion 15 relative to the first grip portion 14, the control hose 18 can displaced on the sliding hose 12. The first grip member 14 is formed with a longitudinal channel 19 joining the lumen of the sliding hose 12 and connecting with a connecting element 20 of grip member 14. Connecting element 20 is provided with an external thread 21 and an annular elastomeric ring 22 arranged internally of element 20. Connecting element 20 is suited for screw-attachment of a connector piece 23 to be used for application of a syringe 24 (FIG. 1) or insertion of a guide wire 25 (FIG. 3).

The first grip member 14 comprises a radially projecting grip 26 and the second grip member 15 likewise comprises a radially projecting grip 27. By pulling the grip 27 toward the grip 26, the control hose 18 can be pulled back on the sliding hose 12.

Figure 2:
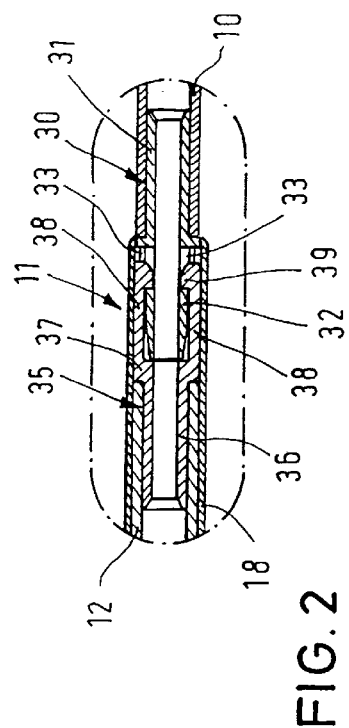
FIG. 2 is an enlarged view of the detail II from FIG. 1.
Figure 5:
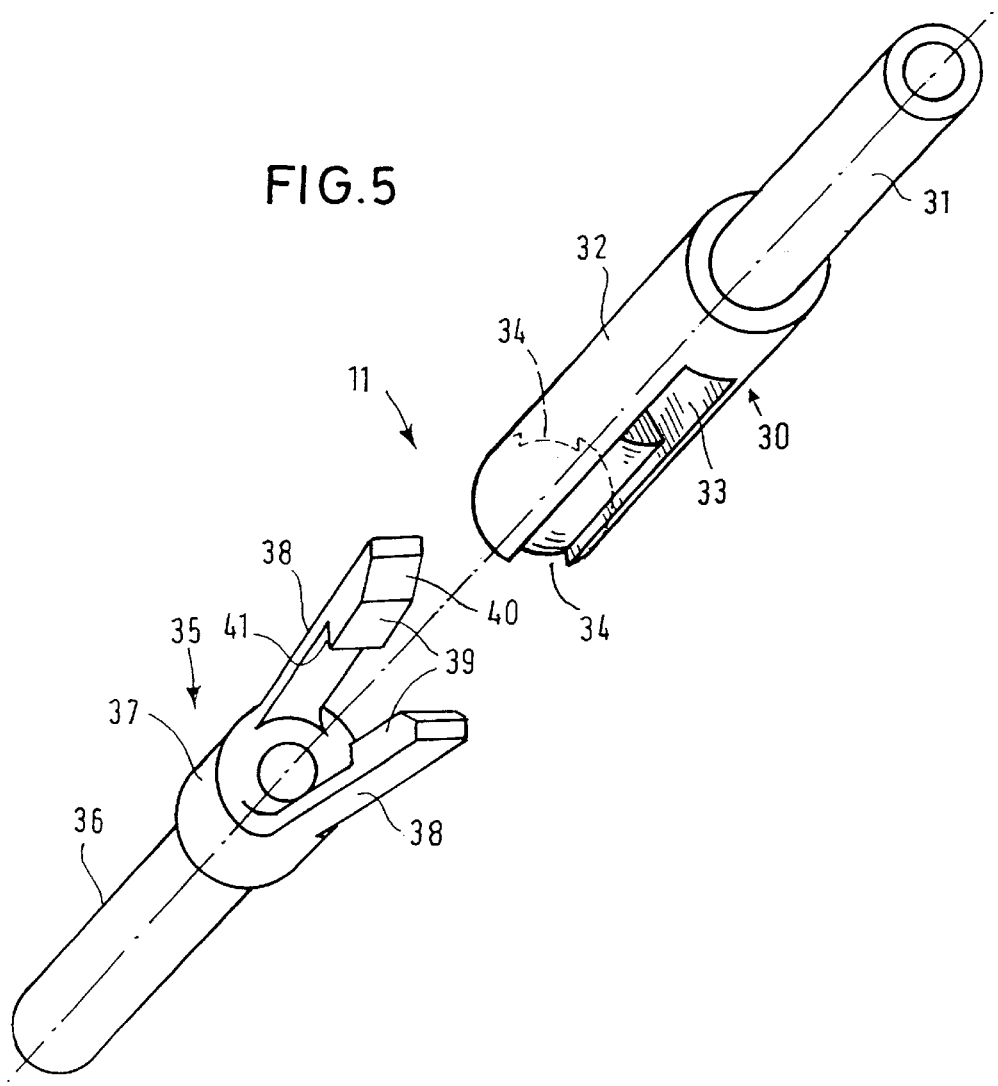
FIG. 5 is a perspective schematic view of the coupling device.

FIG. 2 is an enlarged partial view showing the coupling device 11. Coupling device 11 comprises a first coupling piece 30 having a tubular projection 31 extending into and fixed within ureteral catheter 10. Tubular projection 31 is joined by a larger-diametered headpiece 32 provided with two diametrically opposed recesses 33. Longitudinal guide grooves 34 are formed to lead into these recesses 33 as shown in FIG. 5.

Inserted in the distal end of sliding hose 12 is a coupling member 35 comprising a tubular projection 36 and a headpiece 37 arranged externally of sliding hose 12. The headpiece 37 has two legs 38 extending therefrom, each provided with a hook 39 on its free end. The hooks 39 are each formed with an inclined flank 40 and an upright flank 41. The hooks 39 are biased outwardly, i.e. they tend to spread apart according to FIG. 5. When the coupling members 30,35 are shifted onto each other for mutual engagement as illustrated in FIG. 2, the hooks 39 will enter the recesses 33 at the time that the control hose 18 exerts a force pressing the legs 38 inwardly. Conversely, when the control hose 18 is pulled back, the legs 38 will spread apart and the hooks 39 will leave the recesses 33. For this purpose, the coupling device 11 is given a bias in the release direction.

FIG. 1 shows the ureteral catheter 10 after having been coupled to the sliding hose 12 by means of the coupling device 11. In this situation, control hose 18 is already in an advanced position, thus covering the elastic legs 38 and securing them in the locked condition.

As illustrated in FIG. 3, the guide wire 25 is inserted through connector piece 23 and handling device 13 into sliding hose 12 and ureteral catheter 10, so that the latter is straightened to assume a linear orientation. Subsequently, the guide wire 25 can be fixed in the predetermined position within the handling device 13 by screwing the connector piece 23 tightly into place. Thereby, the elastomeric ring 22 is axially compressed with a resultant decrease of the size of its opening, so that the guide wire 25 is clamped in position in the elastomeric ring 22. In this manner, the connector piece 23 acts also as a tensioning means for clamping the guide wire 25.

Figure 4:
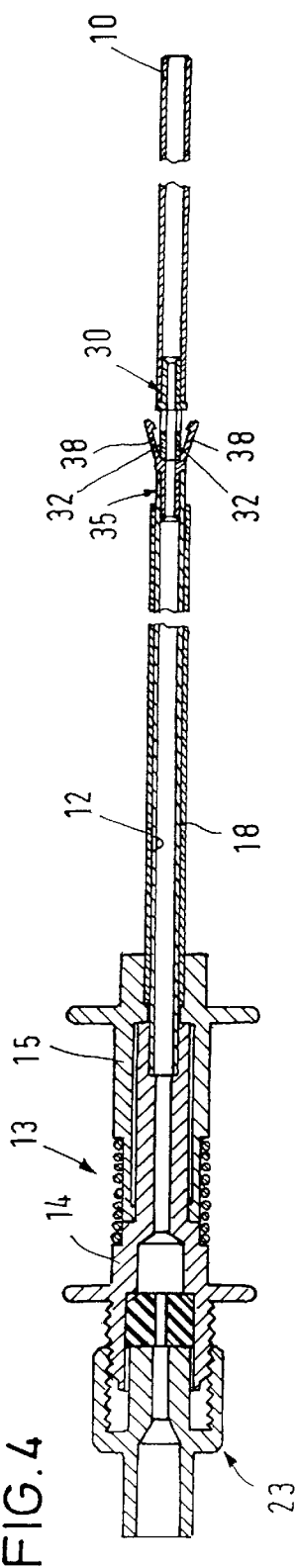
FIG. 4 is a longitudinal sectional view of the device in the condition wherein the ureteral catheter is being detached from the sliding hose.

In the condition shown in FIG. 3, the device is inserted into the patient's body through a cystoscope while the ureteral catheter 10 is placed in the ureter. Then, as shown in FIG. 4, the handling device 13 is actuated by pulling the second grip member 15 toward the first grip member 14, thus tensioning the spring 16. Thereby, the control hose 18 is pulled back to release the coupling device 11 and cause the legs 38 to spread outward in a self-acting manner. Now, the handling device 13 can be pulled back together with sliding hose 12 and control hose 18 while the ureteral catheter 10 will remain in the ureter.

Should the placement of the catheter be performed without use of a guide wire 25, an X-ray contrast medium can be introduced into sliding hose 12 and ureteral catheter 10 by use of the syringe 24, so that the placing of the catheter can be controlled in the X-ray picture.

Instead of inserting the guide wire 25 subsequently, it is also possible, by way of alternative, to first insert the guide wire into the patient's body and then to shift the above described device over the guide wire.

What is claimed is:

1. A ureter drainage device comprising a ureteral catheter (10), a sliding hose (12) adapted to be coupled to a proximal end of the catheter (10); and a control hose (18) adapted to be mounted over the sliding hose (12); the ureteral catheter (10) and the sliding hose (12) including mutually engaging coupling elements (33,38), at least one coupling element (38) provided on the sliding hose (12) being radially outwardly biased in the release direction and being retained in the engagement position by the control hose (18) covering said at least one coupling element (38), a handling device (13) including two grip members (14,15) biased away from each other in the longitudinal direction and arranged to be displaced in the longitudinal direction, one of the grip members (14,15) being connected to the sliding hose (12), and another one of the grip members (14, 15) being connected to the control hose (18).

2. The ureter drainage device according to claim 1, wherein the coupling element (38) of the sliding hose (12) comprises at least one distally projecting leg with a hook (39) formed on its end, and wherein the coupling element (33) of the ureteral catheter (10) has a recess formed therein for receiving the hook (39).

3. The ureter drainage device according to claim 1, wherein the proximal end (10a) of the ureteral catheter (10) comprises an inserted coupling member (30).

4. The ureter drainage device according to claim 1, wherein the coupling element (38) of the sliding hose (12) is provided as a barb configured to lock into a recess (33) of the ureteral catheter (10) when the coupling elements (33, 38) are shifted onto each other.

5. The ureter drainage device according to claim 1, wherein the grip members (14,15) comprise laterally projecting grips (26,27).

* * * * *